US011224351B2

(12) United States Patent
Choi et al.

(10) Patent No.: US 11,224,351 B2
(45) Date of Patent: *Jan. 18, 2022

(54) WEARABLE DEVICE

(71) Applicant: AMOGREENTECH CO., LTD., Gyeonggi-do (KR)

(72) Inventors: Hyung-Suk Choi, Gyeonggi-do (KR); Seung Yun Rho, Gyeonggi-do (KR)

(73) Assignee: AMOGREENTECH CO., LTD., Gyeonggi-Do (KR)

( * ) Notice: Subject to any disclaimer, the term of this patent is extended or adjusted under 35 U.S.C. 154(b) by 71 days.

This patent is subject to a terminal disclaimer.

(21) Appl. No.: 15/570,277

(22) PCT Filed: Apr. 1, 2016

(86) PCT No.: PCT/KR2016/003395
§ 371 (c)(1),
(2) Date: Oct. 27, 2017

(87) PCT Pub. No.: WO2016/175468
PCT Pub. Date: Nov. 3, 2016

(65) Prior Publication Data
US 2018/0132738 A1    May 17, 2018

(51) Int. Cl.
*A61B 5/00* (2006.01)
*A61B 5/024* (2006.01)
(Continued)

(52) U.S. Cl.
CPC .......... *A61B 5/02438* (2013.01); *A61B 5/681* (2013.01); *H01M 10/0436* (2013.01);
(Continued)

(58) Field of Classification Search
CPC ............... A61B 5/02438; A61B 5/681; A61B 2560/0462; A61B 2560/0214;
(Continued)

(56) References Cited

U.S. PATENT DOCUMENTS 5,889,737 A * 3/1999 Alameh ................. G04C 10/00
368/204
9,367,087 B1 * 6/2016 Townsend ............... G06F 1/163
(Continued)

FOREIGN PATENT DOCUMENTS

| JP | 2006-333058 A | 12/2006 | |
|---|---|---|---|
| KR | 10-2001-0018492 A | 3/2001 | |
| KR | 20-0437635 Y1 | 12/2007 | |
| KR | 200437635 Y1 * | 12/2007 | |
| WO | WO-2012140709 A1 * | 10/2012 | ........ H01M 10/052 |

OTHER PUBLICATIONS

International Search Authority/KR, International Search Report dated Jul. 26, 2016 in International Patent Application Mo. PCT/KR2016/003395 (with English translation), 4 pages.

*Primary Examiner* — Rex R Holmes
*Assistant Examiner* — Sana Sahand
(74) *Attorney, Agent, or Firm* — Masuvalley & Partners (57) ABSTRACT

A wearable device is provided. The wearable device according to one embodiment of the present invention includes a body member including a heartbeat sensor, a first band member and a second band member respectively coupled to both ends of the body member, and a flexible battery having a portion accommodated inside the body member and both remaining ends accommodated inside the first band member and the second band member.

9 Claims, 8 Drawing Sheets

(51) Int. Cl.
*H01M 10/04* (2006.01)
*H02J 50/10* (2016.01)
*H02J 7/02* (2016.01)
*H01M 10/42* (2006.01)
*H01M 50/116* (2021.01)
*H01M 50/209* (2021.01)
*H04B 1/3827* (2015.01)
*H04B 1/3883* (2015.01)

(52) U.S. Cl.
CPC ....... *H01M 10/425* (2013.01); *H01M 50/116* (2021.01); *H01M 50/209* (2021.01); *H02J 7/025* (2013.01); *H02J 50/10* (2016.02); *A61B 2560/0214* (2013.01); *A61B 2560/0462* (2013.01); *H01M 2220/30* (2013.01); *H04B 1/385* (2013.01); *H04B 1/3883* (2013.01)

(58) Field of Classification Search
CPC ...... G04G 17/06; G04G 17/00; G04G 17/083; G04G 17/04; G06F 1/1635; G06F 1/163; H01M 10/0468; H01M 10/0481; H01M 10/058; H01M 50/116; H01M 50/209; H01M 10/425; H01M 10/0436; H01M 50/10; H01M 10/0585; H01M 50/256; H01M 10/0525; H01M 50/124; H01M 50/20; H02J 50/10; H02J 50/12; H02J 50/005; H02J 7/025; H02J 7/0044; G04B 37/14; G04C 10/00; A44C 5/0053; A44C 5/14; A44C 5/2009; Y02E 60/10
See application file for complete search history.

(56) References Cited

U.S. PATENT DOCUMENTS

| | | | | |
|---|---|---|---|---|
| 9,798,356 B2* | 10/2017 | Nakayama | .............. | G06F 1/163 |
| 9,943,724 B2* | 4/2018 | Mestas | ................ | A63B 24/0062 |
| 10,203,726 B2* | 2/2019 | Rho | .................... | H04M 1/0268 |
| 10,938,059 B2* | 3/2021 | Rho | .................... | H01M 10/052 |
| 2005/0096556 A1* | 5/2005 | Hsieh Chen | ....... | A61B 5/02438 |
| | | | | 600/509 |
| 2011/0125037 A1* | 5/2011 | Iijima | ................ | A61B 5/02438 |
| | | | | 600/500 |
| 2012/0244408 A1* | 9/2012 | Huang | ................. | H01M 2/1061 |
| | | | | 429/127 |
| 2013/0101884 A1* | 4/2013 | Ueda | ................. | H01M 10/0583 |
| | | | | 429/127 |
| 2013/0231574 A1* | 9/2013 | Tran | ..................... | A61B 5/0022 |
| | | | | 600/479 |
| 2014/0218852 A1* | 8/2014 | Alcazar | ................... | G06F 1/163 |
| | | | | 361/679.03 |
| 2014/0246917 A1* | 9/2014 | Proud | ..................... | H02J 17/00 |
| | | | | 307/104 |
| 2014/0378853 A1* | 12/2014 | McKinney | ......... | A61B 5/02438 |
| | | | | 600/509 |
| 2015/0173675 A1* | 6/2015 | Shimizu | ................. | A61B 5/721 |
| | | | | 600/476 |
| 2015/0313542 A1* | 11/2015 | Goldberg | ............. | A61B 5/0205 |
| | | | | 600/384 |
| 2015/0333302 A1* | 11/2015 | Johns | ................... | H01M 2/1066 |
| | | | | 429/127 |
| 2016/0006201 A1* | 1/2016 | Kim | ................... | H01R 13/6205 |
| | | | | 439/37 |
| 2016/0218327 A1* | 7/2016 | Takahashi | ........... | H01M 2/0275 |
| 2017/0005504 A1* | 1/2017 | Rho | ........................ | H02J 7/025 |

* cited by examiner

WEARABLE DEVICE

RELATED APPLICATIONS

This application is the U.S. National Phase application under 35 U.S.C. § 371 of International Patent Application No. PCT/KR2016/003395 filed on Apr. 1, 2016, which claims priority to Korean Patent Application No. 10-2015-0059191 filed on Apr. 27, 2015, and Korean Patent Application No. 10-2016-0039789 filed on Mar. 31, 2016, which are hereby expressly incorporated by reference in their entirety for all purposes.

TECHNICAL FIELD

The present invention relates to a wearable device, and more particularly, to a wearable device capable of detecting a bio-signal of a user.

BACKGROUND ART

A portable terminal may be configured to perform various functions. Examples of such various functions include data and voice communication functions, a function of taking a photograph or a moving picture, a voice storage function, a function of playing a music file using a speaker system, and a function of displaying an image or video.

When a portable terminal is possessed by being carried in a bag or the like, there is an inconvenience of having to take out and use the portable terminal to make a call or use a message function, and in some cases, a phone is not answered or a message is not noticed due to not hearing a vibration or ringtone of the possessed portable terminal in the bag. To prevent this, a user wears a wearable device and checks a notification event for a call and a message in real time.

Generally, in such a wearable device, a battery for operating the device is embedded only inside a main body which is relatively smaller than a portable terminal. Consequently, because a power supply amount is limiting, a use time is short, and there is an inconvenience of having to frequently charge the wearable device. Further, a separate charging dock or charging cable may be required for charging the wearable device.

Also, when a battery is embedded in a band, presence of a portion for electrically connecting the main body to the band is inevitable, and it is highly likely that foreign substances, moisture, and the like are introduced into the wearable device from outside via the portion. Particularly, moisture introduced via the connecting portion may cause the occurrence of current leakage or oxidation of the connecting portion.

DISCLOSURE

Technical Problem

The present invention has been devised in consideration of the above aspects, and it is an object of the present invention to provide a wearable device whose use time is able to be increased.

Also, it is another object of the present invention to provide a wearable device that is able to be easily charged.

Technical Solution

To achieve the above objects, the present invention provides a wearable device including a body member including a heartbeat sensor, a first band member and a second band member respectively coupled to both ends of the body member, and a flexible battery having a portion accommodated inside the body member and both remaining ends accommodated inside the first band member and the second band member.

According to an exemplary embodiment of the present invention, the wearable device may include a circuit board disposed inside the body member and disposed above the flexible battery and a connecting member having one end coupled to the circuit board and the other end disposed below the flexible battery and electrically connected to the heartbeat sensor.

In the connecting member, a portion of an edge of the portion connected to the heartbeat sensor may be cut so that the portion connected to the heartbeat sensor is able to move relative to a peripheral portion.

A seating portion in which a portion corresponding to the heartbeat sensor is perforated may be formed at a bottom surface of the body member.

The wearable device may include a wireless power transmission unit disposed inside the body member to wirelessly receive power and supply power to the flexible battery.

The wireless power transmission unit may include a power receiving antenna disposed at a surface opposite a surface of the connecting member connected to the heartbeat sensor.

The connecting member may be a flexible printed circuit board.

The connecting member may be folded at least once such that a portion thereof is disposed between the circuit board and the flexible battery.

A length of the portion of the connecting member disposed between the circuit board and the flexible battery may be greater than twice a width of the circuit board.

The wireless power transmission unit may receive power using a magnetic resonance method or a magnetic induction method.

Each of the first band member and the second band member may include an accommodating portion disposed at the portion coupled to the body part and configured to accommodate a portion of an end of the flexible battery.

The portion of the flexible battery accommodated in the accommodating portion may be entirely or partially corrugated.

The portion of the flexible battery accommodated in the body member may have a plate shape.

The wearable device may include a communication unit configured to transmit heartbeat information measured by the heartbeat sensor to outside.

The flexible battery may include an electrode assembly and a cover member configured to seal the electrode assembly with an electrolyte, and the electrode assembly and the cover member may be formed such that patterns for contraction and relaxation in a longitudinal direction are disposed to be coincident with each other when the flexible battery is bent.

The pattern may be provided such that a plurality of crests and a plurality of troughs are alternately formed in the longitudinal direction, and the crests and the troughs may have an arc-shaped cross section, a polygonal cross section, or a combination thereof.

Advantageous Effects

According to the present invention, the both remaining ends of the flexible battery are respectively accommodated in the first band member and the second band member. That is, a single flexible battery is embedded across inner portions of the body member, the first band member, and the second band member. Accordingly, in comparison to a general wearable device in which a battery is embedded only in a body member, a size of the flexible battery may be increased in the wearable device according to the present invention. Consequently, a capacitance of the flexible battery is also increased such that a use time of the wearable device according to one embodiment of the present invention can be increased.

Also, the use time of the wearable device according to one embodiment of the present invention can be increased without increasing a thickness or size of the wearable device.

Further, a user can promptly measure a heartbeat while wearing the wearable device.

Also, unlike a conventional wearable device, because the wearable device according to the present invention can be charged using a wireless charger without connecting a charging cable to the body member, convenience in use can be improved.

Also, because a charging port, which is an essential configuration for connecting a charging cable in a conventional wired charging method, is not required, a failure caused by foreign substances and moisture can be prevented. Therefore, handling and managing the wearable device by the user can be extremely facilitated.

Furthermore, because the wearable device according to the present invention does not include a charging port through which the inner portion of the body member may be exposed to the outside, airtightness is improved and a structure for waterproofing can be easily implemented.

Also, because the wearable device according to the present invention can utilize an additional space as much as a space that is conventionally occupied by a charging port, the design freedom can be improved by adding additional functions, making innovative design changes, or the like.

MODES OF THE INVENTION

Hereinafter, embodiments of the present invention will be described in detail with reference to the accompanying drawings so that one of ordinary skill in the art to which the present invention pertains can easily practice the present invention. The present invention may be implemented in various different forms and is not limited to the embodiments described herein. Parts unrelated to the description are omitted from the drawings to clearly describe the present invention, and like or similar elements are denoted by like reference numerals throughout the specification.

Figure 1:
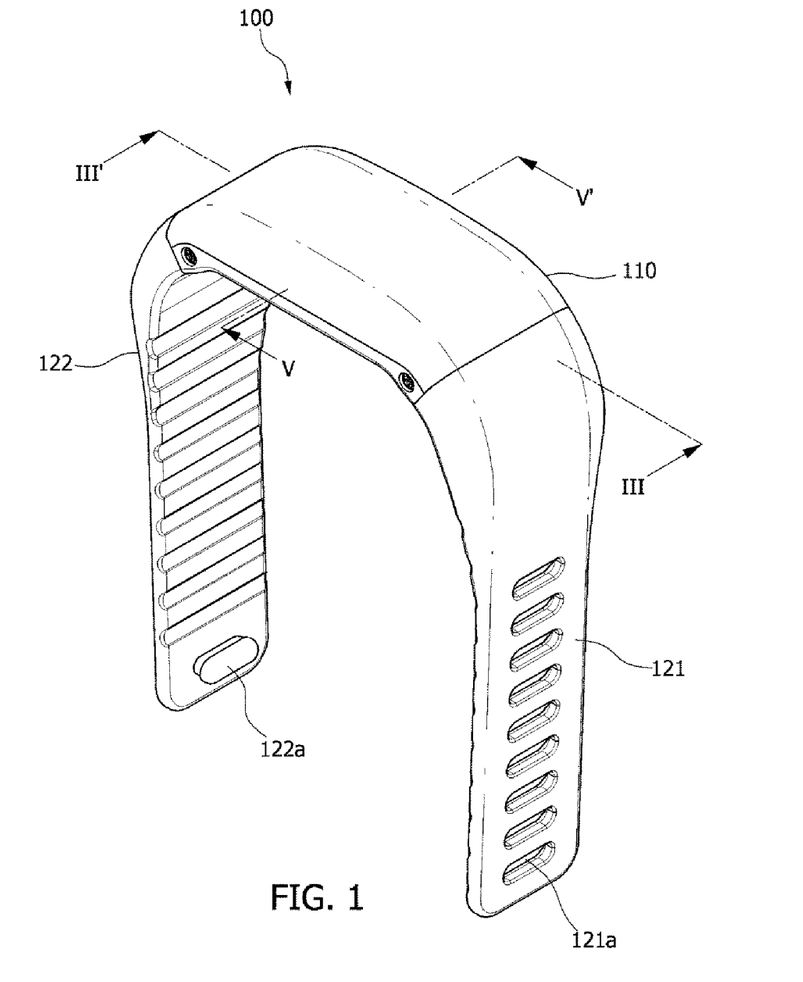
FIG. 1 is a view illustrating a wearable device according to one embodiment of the present invention.
Figure 2:
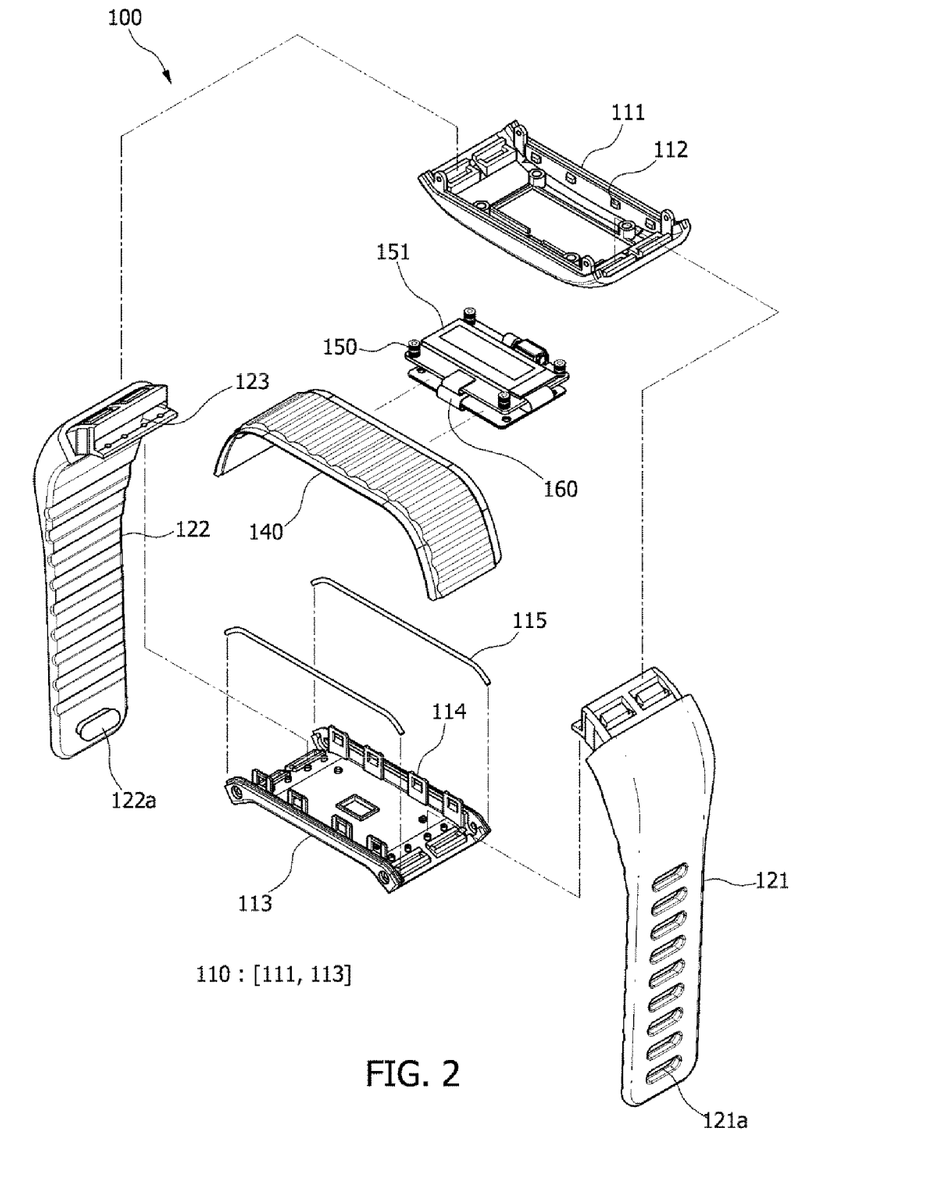
FIG. 2 is an exploded perspective view of the wearable device of FIG. 1.
Figure 3:
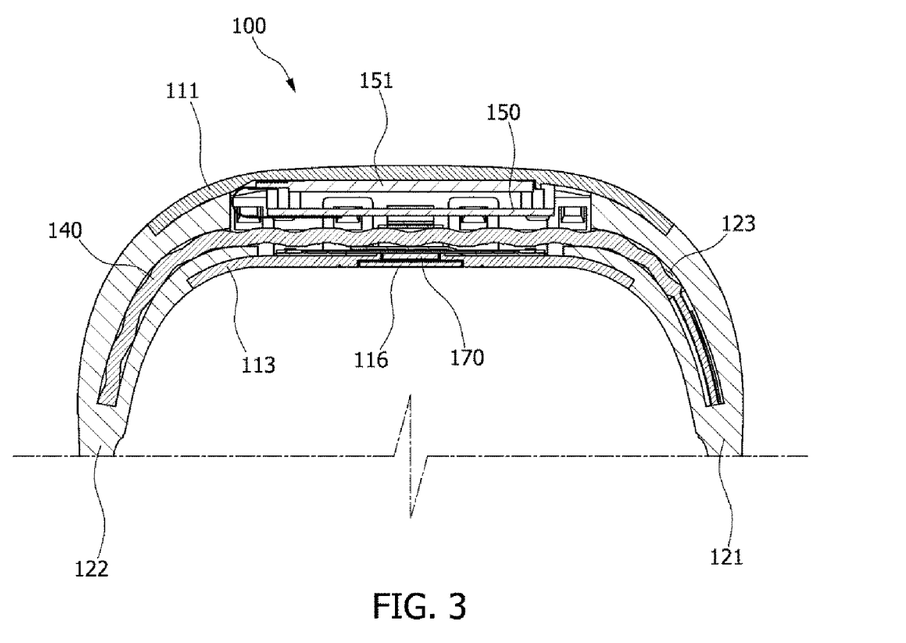
FIG. 3 is a cross-sectional view taken along line of the wearable device of FIG. 1.

As illustrated in FIGS. 1 to 3, a wearable device 100 according to one embodiment of the present invention includes a body member 110, a first band member 121, a second band member 122, and a flexible battery 140.

The body member 110 includes a heartbeat sensor 170. The heartbeat sensor 170 measures a heartbeat of a user. Accordingly, the user may promptly measure his or her heartbeat while wearing the wearable device 100 according to one embodiment of the present invention.

For example, the body member 110 may include an upper portion 111 and a lower portion 113. The flexible battery 140 which will be described below and the a wireless power transmission unit 130 and a communication unit which will be described below may be disposed between the upper portion 111 and the lower portion 113. For example, a coupling structure between the upper portion 111 and the lower portion 113 may have locking steps 112 formed at an inner surface of the upper portion 111 and locking rings 114 formed at an inner surface of the lower portion 113.

The numbers and positions of the locking steps 112 and the locking rings 114 may correspond one-to-one with each other. The upper portion 111 and the lower portion 113 may also be fastened using a bolt to facilitate maintenance and repair of the wearable device 100 according to one embodiment of the present invention and improve a fastening force thereof.

A seal ring 115 may be interposed between portions of the body member 110 at which the upper portion 111 and the lower portion 113 are adhered to each other. The seal ring 115 may be formed in a linear shape and disposed along the portion at which the upper portion 111 and the lower portion 113 are adhered to each other. A material of the seal ring 115 may be, for example, rubber, silicone, or synthetic resin. The seal ring 115 may seal a gap between the upper portion 111 and the lower portion 113 and prevent introduction of moisture or foreign substances into the body member 110 from the outside.

The first band member 121 and the second band member 122 are respectively coupled to both ends of the body member 110. The first band member 121 and the second band member 122 allow the body member 110 to be stably worn on a part of the user's body, e.g., the user's wrist.

For example, a fastening structure between the first band member 121 and the second band member 122 has a plurality of coupling holes 121a formed at predetermined intervals in the longitudinal direction in the first band member 121. Also, a coupling protrusion 122a is formed at one side surface of an end of the second band member 122. The coupling protrusion 122a may be coupled to any one of the plurality of coupling holes 121a in accordance with a circumference of the user's wrist.

However, the fastening structure between the first band member 121 and the second band member 122 is not limited to the above structure and may be any structure as long as the structure allows the first band member 121 and the second band member 122 to remain stably coupled to each other.

A material of the first band member 121 and the second band member 122 may be, for example, thermoplastic polyurethane (TPU). Accordingly, the first band member 121 and the second band member 122 may be freely deformed by an external force and adhered to the user's wrist.

In this way, by the first band member 121 and the second band member 122 being formed with TPU that may be compressed and deformed by an external force, the first band member 121 and the second band member 122 may prevent generation of a gap at a portion coupled to the body member 110 and improve airtightness.

However, the material of the first band member 121 and the second band member 122 is not limited to TPU and may be any material as long as the material is restorable to its initial shape after being deformed by an external force.

The flexible battery 140 supplies a current to an electronic component of the wearable device 100 according to one embodiment of the present invention. The flexible battery 140 may be a rechargeable secondary battery, and this will be described in detail below.

A portion of the flexible battery 140 is accommodated inside the body member 110, and both remaining ends thereof are accommodated inside the first band member 121 and the second band member 122.

For example, an intermediate portion of the flexible battery 140 is accommodated in the body member 110. Also, the both remaining ends of the flexible battery 140 are respectively accommodated in the first band member 121 and the second band member 122. That is, the single flexible battery 140 is embedded across inner portions of the body member 110, the first band member 121, and the second band member 122.

In comparison to a structure in which a general battery is embedded only in the body member 110, a length of the flexible battery 140 may be increased in the above structure. Consequently, a capacitance of the flexible battery 140 is also increased such that a use time of the wearable device 100 according to one embodiment of the present invention may be increased.

Unlike this, in the case of a conventional wearable device, because a thickness or size of a battery has to be increased to increase a use time of the wearable device, a thickness or size of the wearable device is inevitably increased. However, as described above, the use time of the wearable device 100 according to one embodiment of the present invention may be increased without increasing a thickness or size of the wearable device 100.

Each of the first band member 121 and the second band member 122 may include an accommodating portion 123 disposed at the portion coupled to the body member 110 and configured to accommodate a portion of an end of the flexible battery 140. The accommodating portion 123 may be formed of a size that is relatively larger than that of the flexible battery 140. This is to allow the flexible battery 140 to be freely deformed within the accommodating portion 123.

When the user wears the wearable device 100 according to one embodiment of the present invention, the first band member 121 and the second band member 122 may be deformed by an external force. A corrugated portion of the flexible battery 140 may be freely bent with deformation of the first band member 121 and the second band member 122.

For this, for example, the flexible battery 140 may be formed to have a length. Also, a portion of the flexible battery 140 accommodated in the accommodating portion 123 may be entirely or partially corrugated. For example, only a portion of the flexible battery 140 accommodated in the accommodating portion 123 may be corrugated.

Also, the flexible battery 140 may be formed such that, among the portions of the flexible battery 140 accommodated in the first band member 121 and the second band member 122, only a portion at which the first band member 121 and the second band member 122 are deformed by an external force is corrugated. However, embodiments are not limited thereto, and the flexible battery 140 may also be formed such that the entire flexible battery 140 is corrugated.

Unlike this, a portion of the flexible battery 140 accommodated in the body member 110 may have a plate shape, and the remaining portions thereof may be corrugated. Accordingly, because a total thickness of the body member 110 may be decreased as much as an increase in a thickness of the flexible battery 140 due to the corrugation, a wearing sensation of the wearable device 100 according to one embodiment of the present invention as well as an appearance thereof may be improved.

The wearable device 100 according to one embodiment of the present invention will be described in more detail. The wearable device 100 may include the wireless power transmission unit 130, a communication unit (not illustrated), a circuit board 150, and a connecting member 160.

The wireless power transmission unit 130 is disposed inside the body member 110 to wirelessly receive power and supply power to the flexible battery 140. That is, the above-described flexible battery 140 may be charged by the wireless power transmission unit 130. The wireless power transmission unit 130 may receive power using, for example, a magnetic resonance method or a magnetic induction method, but embodiments are not limited thereto, and any method may be used as long as the method is capable of wirelessly receiving power.

The communication unit transmits heartbeat information measured by the heartbeat sensor 170 to outside. The communication unit may be, for example, a Bluetooth module. Accordingly, when the wearable device 100 according to one embodiment of the present invention measures heartbeat information in a state in which the user is carrying a portable terminal and wearing the wearable device 100 according to one embodiment of the present invention, the measured heartbeat information may be transmitted to the portable terminal.

Unlike this, the communication unit may also be able to transmit heartbeat information via a wireless network. The wireless network may be, for example, a mobile communication wireless-based data service network such as long term evolution (LTE), LTE-Advance (LTE-A), World Interoperability for Microwave Access (WiMAX), wireless broadband internet (WiBro), high speed packet access (HSPA), high speed uplink packet access (HSUPA), high speed downlink packet access (HSDPA), wideband code division multiple access (WCDMA), 1x Evolution-Data Optimized (EV-DO), general packet radio service (GPRS), and Enhanced Data GSM Environment (EDGE) or Institute of Electrical and Electronics Engineers (IEEE) 802. 11 b/g/n/ac, but is not limited thereto.

By the communication unit transmitting heartbeat information via the wireless network as above, the heartbeat information may be transmitted to and stored in a server or terminal located at a different position from the wearable device 100 according to one embodiment of the present invention. The user may check the heartbeat information stored in the server by using various terminals such as a laptop and a tablet.

The circuit board 150 is disposed inside the body member 110 and is disposed above the flexible battery 140. Various elements for operating the wearable device 100 according to one embodiment of the present invention may be mounted on the circuit board 150.

For example, a communication chip that may serve as the above-described communication unit may be mounted on the circuit board 150. An overcharge protection circuit configured to prevent an overcharge of the flexible battery 140 may also be mounted on the circuit board 150. Furthermore, a vibration unit 152 that allows the user to feel vibration may also be mounted on the circuit board 150. A global positioning system (GPS) module and a near-field communication (NFC) tag may also be mounted on the circuit board 150. A memory element configured to store the heartbeat information measured by the heartbeat sensor 170 may also be mounted on the circuit board 150.

A control unit configured to control an overall operation of the wearable device 100 according to the present invention, the above-described communication unit, and the memory element may be integrated and implemented in a single application processor (AP).

The connecting member 160 electrically connects the circuit board 150 to the heartbeat sensor 170. For this, one end of the connecting member 160 is coupled to the circuit board 150. The other end of the connecting member 160 is disposed below the flexible battery 140 and is electrically connected to the heartbeat sensor 170.

As a method of electrically connecting the heartbeat sensor 170 and the connecting member 160, the heartbeat sensor 170 may be mounted on a surface of the connecting member 160 by a surface mount technology, but embodiments are not limited thereto.

The wearable device 100 according to one embodiment of the present invention may include a display module 151. The display module 151 may be disposed on the circuit board 150. The display module 151 may output an operation state of the wearable device 100 according to one embodiment of the present invention.

For example, the display module 151 may be a flat display panel disposed to be spaced a predetermined distance apart from the upper portion 111 of the body member 110. Unlike this, as another example, the display module 151 may be a flexible display panel.

Here, an outer surface of the upper portion 111 of the body member 110 may be a curved surface. An inner surface of the upper portion 111 of the body member 110 may also be a curved surface. For example, a cover window may be formed at the outer surface of the upper portion 111.

The flexible display panel may be attached to the cover window in the state of being bent. Accordingly, by an image being output on the flexible display panel in a state in which the flexible display panel is bent, the user may clearly view the image output on the flexible display panel regardless of an angle at which the user gazes at the image while wearing the wearable device 100 according to one embodiment of the present invention. Because the flexible display panel may be a known flexible display panel, a detailed description thereof will be omitted.

In the above-described wearable device 100 according to one embodiment of the present invention, the upper portion 111 of the body member 110, the display module 151, the circuit board 150, the flexible battery 140, the heartbeat sensor 170, and the lower portion 113 of the body member 110 may be sequentially disposed in that order from top to bottom.

In the connecting member 160, a portion of an edge of the portion connected to the heartbeat sensor 170 may be cut so that the portion connected to the heartbeat sensor 170 is able to move relative to a peripheral portion 160b. Accordingly, the heartbeat sensor 170 may relatively move in a direction moving away from or approaching the connecting member 160 while being electrically connected to the connecting member 160. For convenience of description, a portion of the connecting member 160 connected to the heartbeat sensor 170 will be defined as a moving portion 160c, and a periphery of the moving portion 160c will be defined as the peripheral portion 160b.

Accordingly, the heartbeat sensor 170 may be disposed to be adjacent to the flexible battery 140 as much as possible. That is, in comparison to the wearable device 100 in which a portion of the connecting member 160 is not cut, the heartbeat sensor 170 may further decrease a total thickness of the wearable device 100 in the case of the wearable device 100 having the above structure.

Figure 4:
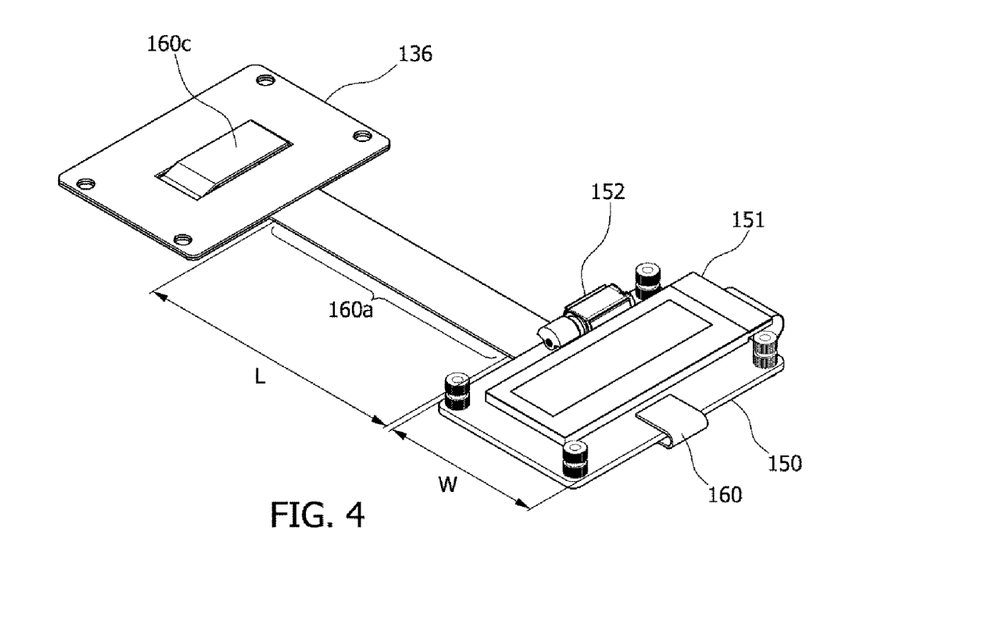
FIG. 4 is a view illustrating a circuit board and a connecting member of the wearable device of FIG. 2.
Figure 5:
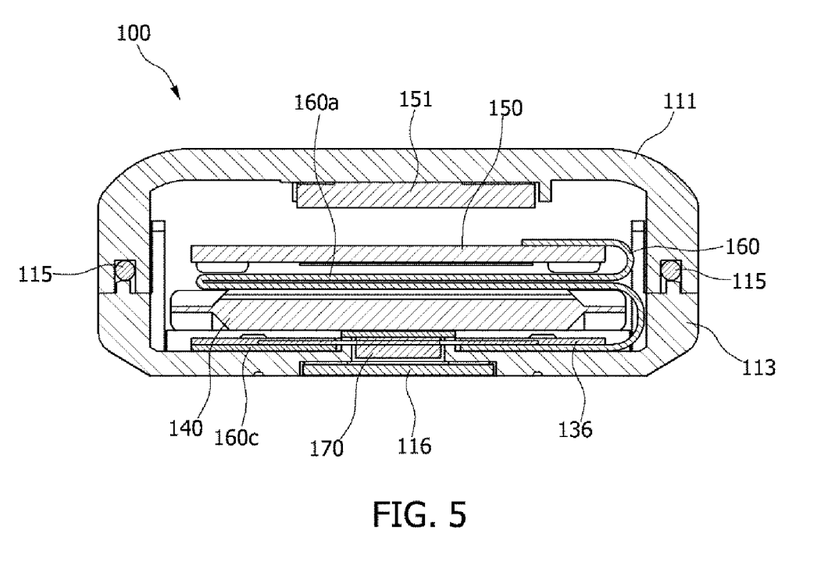
FIG. 5 is a cross-sectional view taken along line V-V' of the wearable device of FIG. 1.
Figure 6:
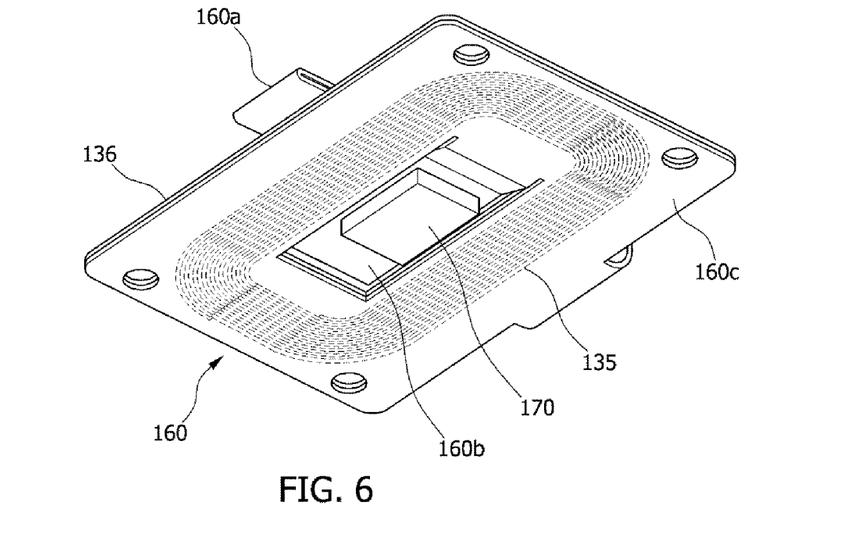
FIG. 6 is a view of the connecting member of the wearable device of FIG. 2 from the bottom.
Figure 7:
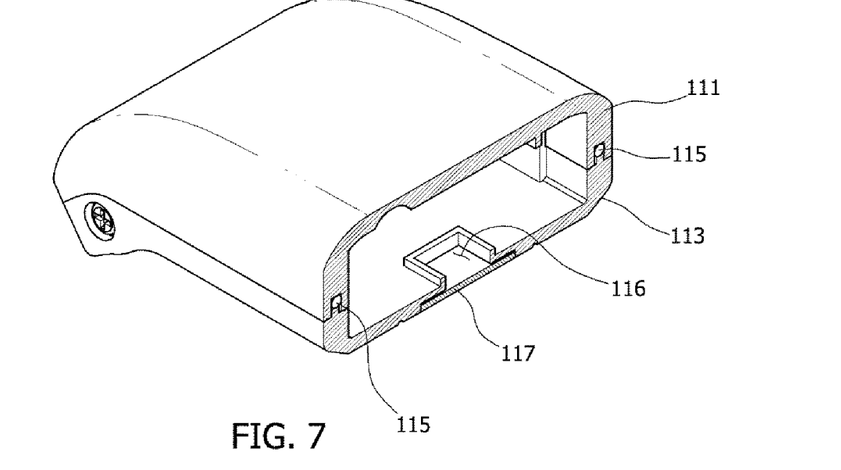
FIG. 7 is a view of the wearable device of FIG. 1 from which a portion of a body member is cut away.

The connecting member 160 may be a flexible printed circuit board (FPCB). Referring to FIGS. 4 to 6, the connecting member 160 may be fold at least once such that the portion 160a thereof is disposed between the circuit board 150 and the flexible battery 140.

For example, an order of assembling the wearable device 100 according to one embodiment of the present invention may be such that the heartbeat sensor 170 may be coupled to the lower portion 113 of the body member 110 in a state in which the heartbeat sensor 170 and the circuit board 150 are connected to the connecting member 160, and then the circuit board 150 may be coupled to the upper portion 111 of the body member 110.

By the circuit board 150 and the heartbeat sensor 170 being sufficiently spaced apart from each other in the process of assembling the upper portion 111 and the lower portion 113, the assembling may be easily performed. For this, a length of the portion 160a of the connecting member 160 disposed between the circuit board 150 and the flexible battery 140 may be greater than twice a width of the circuit board 150.

Here, there is no upper limit to the length of the connecting member 160, and the length may be freely changed in accordance with the design of the wearable device 100 as long as the length does not excessively increase the thickness of the wearable device 100 according to one embodiment of the present invention.

A seating portion 116 in which a portion corresponding to the heartbeat sensor 170 is perforated may be formed at a bottom surface of the body member 110. More specifically, the seating portion 116 may be formed at the lower portion 113 of the body member 110. The seating portion 116 may be formed to be able to accommodate a portion of the heartbeat sensor 170. The heartbeat sensor 170 may be stably seated in the seating portion 116.

For example, the heartbeat sensor 170 may be an optical heartbeat sensor 170. Here, a penetration member 117 formed of a transparent material may be disposed at a portion corresponding to the seating portion 116 at the lower portion 113 of the body member 110. For a smooth operation of the optical heartbeat sensor 170, the penetration member 117 allows a portion of the optical heartbeat sensor 170 to face outward.

The above-described wireless power transmission unit 130 wirelessly receives power from an external power supply device (not illustrated). Here, because the external power supply device may be a known wireless charger, a detailed description of a structure, an operation process, and the like thereof will be omitted.

Figure 8:
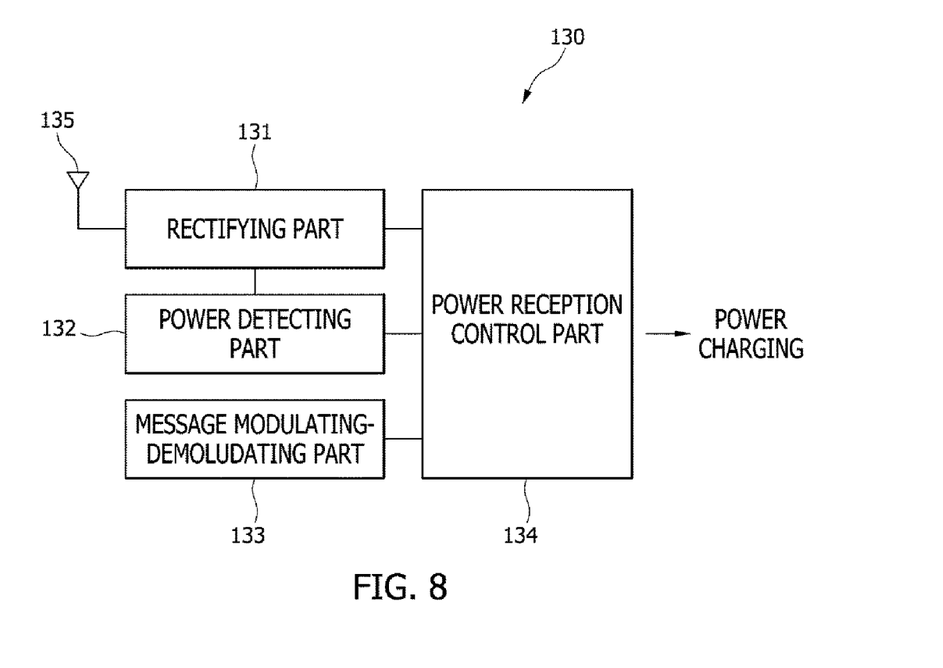
FIG. 8 is a block diagram of a wireless power transmission unit included in the wearable device according to the present invention.

The wireless power transmission unit 130 will be described in more detail. As illustrated in FIG. 8, for example, the wireless power transmission unit 130 may include a rectifying part 131, a power detecting part 132, a message modulating-demodulating part 133, a power reception control part 134, and a power receiving antenna 135.

The rectifying part 131 may perform full-wave rectification to convert an alternating-current wireless power signal received from the power receiving antenna 135 into a direct current. The rectifying part 131 may further include a smoothing circuit for converting a rectified current into a more flat and stable direct current.

The power detecting part 132 may monitor a voltage or current of power rectified by the rectifying part 131.

The message modulating-demodulating part 133 may demodulate a wireless power signal by the power reception control part 134 and use the demodulated wireless power signal to transmit a power control message signal.

The power reception control part 134 may control each element included in the wireless power transmission unit 130.

The power receiving antenna 135 may be formed in various shapes and sizes in accordance with a wireless charging method of the wireless power transmission unit 130.

For example, the power receiving antenna 135 (see FIG. 9) included in the wireless power transmission unit 130 may be disposed at a surface opposite a surface of the connecting member 160 connected to the heartbeat sensor 170.

Figure 9:
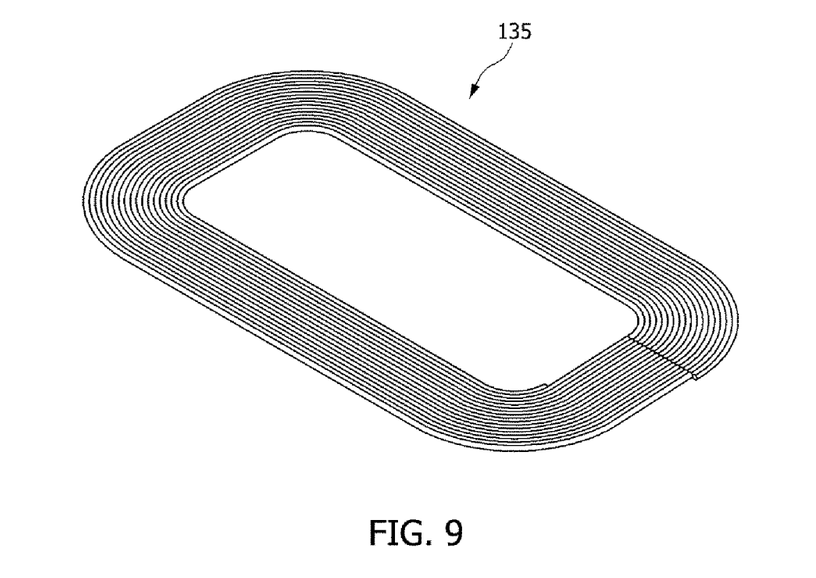
FIG. 9 is a view illustrating a power receiving antenna included in the wireless power transmission unit.
Figure 10:
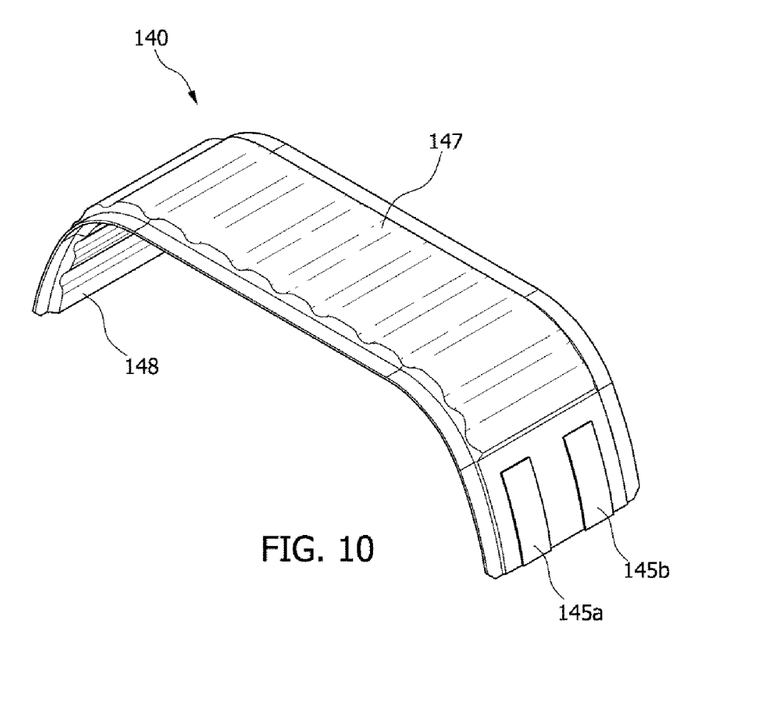
FIG. 10 is a view illustrating a flexible battery of the wearable device according to the present invention.

For example, the power receiving antenna 135 may be formed by patterning a conductor such as copper foil on at least one surface of a synthetic resin or by forming a loop-shaped metal pattern using conductive ink on at least one surface of a synthetic resin.

For example, the power receiving antenna 135 may be an FPCB antenna. The FPCB antenna is formed by printing an antenna pattern on a FPCB.

The power receiving antenna 135 may have a size similar to that of the above-described circuit board 150 or have a size relatively smaller than that of the circuit board 150, but embodiments are not limited thereto.

The power receiving antenna 135 may be formed in the shape of a film as a whole, and an adhesive layer may be formed at both surfaces thereof. Accordingly, one surface of the power receiving antenna 135 may be attached to the connecting member 160, and the other surface thereof may be adhered to another adjacent member. For this, a portion of the connecting member 160 to which the power receiving antenna 135 is attached may be formed in a size corresponding to that of the circuit board 150. By this structure, the assembling of the wearable device 100 according to one embodiment of the present invention may be promptly implemented.

Here, the power receiving antenna 135 may be attached to the peripheral portion 160*b* of the portion of the connecting member 160 electrically connected to the heartbeat sensor 170. That is, the power receiving antenna 135 may be formed such that a portion corresponding to the portion of the connecting member 160 connected to the heartbeat sensor 170 is perforated. Accordingly, as described above, the portion of the connecting member 160 connected to the heartbeat sensor 170 may freely move in a vertical direction relative to the peripheral portion 160*b*.

Although not illustrated, the wearable device 100 according to one embodiment of the present invention may also be configured as a combination type including at least one of a magnetic secure transmission (MST) antenna for MST and a NFC antenna for NFC in addition to the above-described antenna for wireless power transmission.

Here, the wearable device 100 according to one embodiment of the present invention may include a shielding sheet 136. The shielding sheet 136 may be disposed between the power receiving antenna 135 and the flexible battery 140.

As described above, the shielding sheet 136 may be adhered to the power receiving antenna 135 by the adhesive layer formed at one surface of the power receiving antenna 135. The shielding sheet 136 may shield a magnetic field generated by a radio signal induced in the antenna and also focus the magnetic field in a required direction.

The shielding sheet 136 may be a ferrite sheet or an amorphous sheet formed of a plate-shaped member having a predetermined area or may be formed of a hybrid sheet formed by stacking the two. The ferrite sheet may be formed of a sintered ferrite sheet and may consist of MnZn ferrite or NiZn ferrite. Also, the amorphous sheet may be a ribbon sheet including one or more of an amorphous alloy and a nano-crystal grain alloy, and the ribbon sheet may be stacked in multiple layers or flaked and separated into a plurality of fine pieces.

By including the wireless power transmission unit 130 as described above, the wearable device 100 according to the present invention may be charged just by being placed on a charging stand. Consequently, unlike a conventional wearable device, because the wearable device 100 according to the present invention may be charged using a wireless charger without connecting a charging cable to the body member 110, convenience in use may be improved.

Also, because a charging port, which is an essential configuration for connecting a charging cable in a conventional wired charging method, is not required, a failure caused by foreign substances and moisture may be prevented. Also, handling and managing the wearable device 100 by the user may be extremely facilitated. Furthermore, because the wearable device 100 according to the present invention does not include a charging port through which the inner portion of the body member 110 may be exposed to the outside, airtightness is improved and a structure for waterproofing may be easily implemented.

Also, because the wearable device 100 according to the present invention may utilize an additional space as much as a space that is conventionally occupied by a charging port, the design freedom may be improved by adding additional functions, making innovative design changes, or the like.

Figure 11:
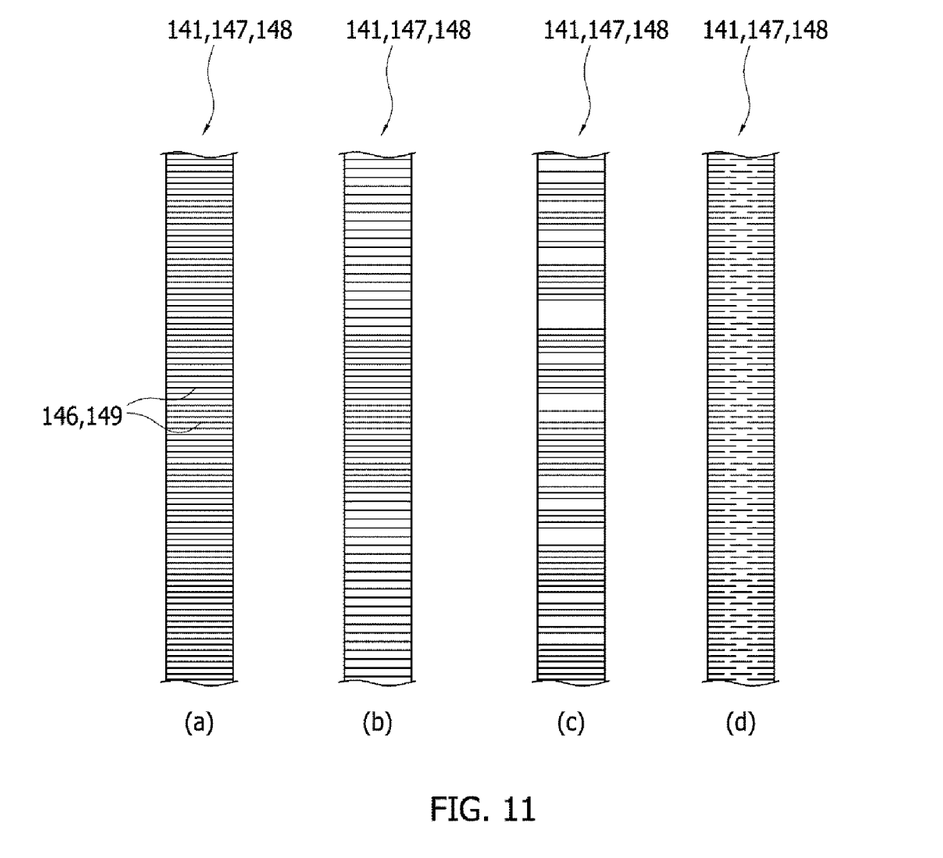
FIG. 11 is a view illustrating examples of various patterns applied to an electrode assembly and a cover member in the flexible battery of FIG. 10 and illustrating various intervals between neighboring troughs or crests.
Figure 12:
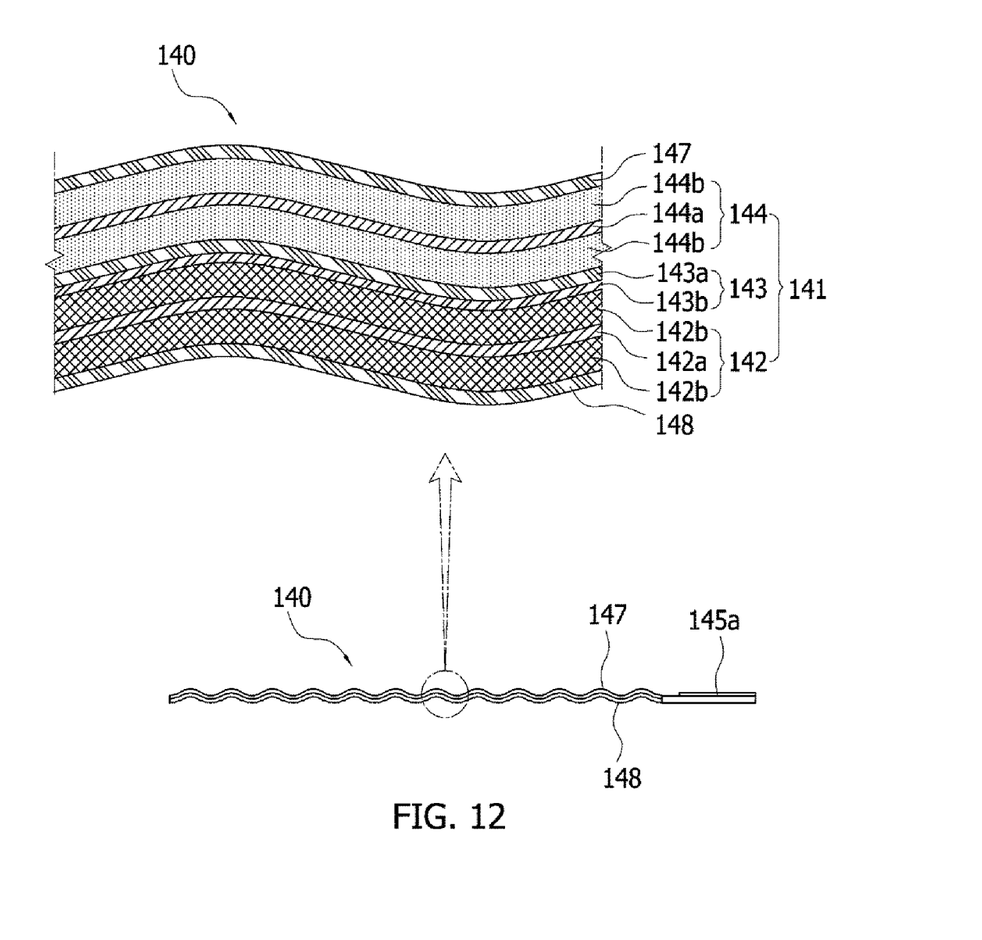
FIG. 12 is a view illustrating an enlarged view of an inner portion of the flexible battery of FIG. 10.

Referring to FIGS. 11 and 12, for example, the above-described flexible battery 140 includes an electrode assembly 141 and cover members 147 and 148, and the electrode assembly 141 is sealed inside the cover members 147 and 148 with an electrolyte.

Here, patterns 146 and 149 for contraction and relaxation in the longitudinal direction are respectively formed at the electrode assembly 141 and the cover members 147 and 148, and a first pattern 149 formed at the cover members 147 and 148 and a second pattern 146 formed at the electrode assembly 141 are formed to have the same directionality.

In this way, because deformation of a base material itself constituting the electrode assembly 141 and the cover members 147 and 148 is prevented or a deformation amount of the base material itself is minimized, the deformation amount of the base material itself that may occur at a bent portion is minimized even when banding occurs such that damage to the electrode assembly 141 and the cover members 147 and 148 or deterioration of performance thereof may be prevented.

Here, the first pattern 149 and the second pattern 146 not only have the same directionality, but also are disposed to be coincident with each other. This is to allow the same behavior to occur in the first pattern 149 and the second pattern 146 at all times.

In this way, by the patterns 146 and 149 for contraction and relaxation in the longitudinal direction that occur during banding being formed in the electrode assembly 141 and the cover members 147 and 148 to be coincident with each other, the electrode assembly 141 and the cover members 147 and 148 may remain in contact or spaced apart by a uniform interval at all times with respect to a total length even when bending in the longitudinal direction occurs in the flexible battery 140. Therefore, the electrolyte sealed with the electrode assembly 141 is evenly distributed throughout the total length such that deterioration of performance as a battery may be prevented.

For this, in the first pattern 149 and the second pattern 146, each of the crests and troughs may be formed in a direction parallel to width directions of the cover members 147 and 148 and the electrode assembly 141, and the crests and troughs may be alternately disposed in the longitudinal directions of the cover members 147 and 148 and the electrode assembly 141. Also, the crests and troughs constituting the first pattern 149 and the second pattern 146 are formed such that the crests are formed at the same position as each other and the troughs are formed at the same position as each other. In this way, the first pattern 149 and the second pattern 146 may be coincident with each other.

Specifically, the crests and troughs of the first pattern 149 and the second pattern 146 may be formed in a direction parallel to a straight line parallel to the width directions of the cover members 147 and 148 and the electrode assembly 141, and the crests and troughs may be repeatedly disposed in the longitudinal direction.

Here, the patterns 146 and 149 may be continuously formed or discontinuously formed in the direction parallel to the width directions of the electrode assembly 141 and the cover members 147 and 148 and may be formed throughout the total lengths of the electrode assembly 141 and the cover members 147 and 148 or may be partially formed throughout partial lengths thereof.

For example, the patterns 146 and 149 of the flexible battery 140 may also be formed at a portion accommodated in the first band member 121 and the second band member 122. Unlike this, the patterns 146 and 149 of the flexible battery 140 may also be formed only at a portion at which the first band member 121 and the second band member 122 are deformed by an external force among the portions of the flexible battery 140 accommodated in the first band member 121 and the second band member 122.

Returning to FIG. 12, the crests and troughs may have an arc-shaped cross-section including a semicircular cross-section, a polygonal cross-section including a triangular or rectangular cross-section, or cross-sections of various shapes in which the arc-shaped cross-section and the polygonal cross-section are combined. Although the crests and troughs may have the same pitch and width, the crests and troughs may also have pitches and widths different from each other.

In this way, even when the cover members 147 and 148 and the electrode assembly 141 are embedded in the flexible battery 140 while being bent, a degree of fatigue applied to the base material itself via the patterns 146 and 149 may be reduced.

The first pattern 149 and the second pattern 146 may be formed such that intervals between neighboring crests or intervals between neighboring troughs are equal to or different from each other, or the first pattern 149 and the second pattern 146 may also be formed such that equal intervals and different intervals are combined.

In addition, although the first pattern 149 formed at the cover members 147 and 148 may be formed throughout the total surfaces of the cover members 147 and 148, the first pattern 149 may also be partially formed throughout the partial surfaces thereof. For example, as described above, the first pattern 149 may be formed only at portions of the cover members 147 and 148 accommodated in the first band member 121 (see FIG. 2) and the second band member 122 (see FIG. 2).

The electrode assembly 141 is sealed inside the cover members 147 and 148 with the electrolyte and includes a positive electrode 142, a negative electrode 144, and a separator 143.

The positive electrode 142 may include a positive electrode current collector 142a and a positive electrode active material 142b, the negative electrode 144 may include a negative electrode current collector 144a and a negative electrode active material 144b, and the positive electrode current collector 142a and the negative electrode current collector 144a may be implemented in the form of a plate-shaped sheet having a predetermined area.

That is, in the positive electrode 142 and the negative electrode 144, the active materials 142b and 144b may be respectively compressed, deposited, or applied to one surface or both surfaces of the current collectors 142a and 144a. Here, the active materials 142b and 144b may be provided throughout the entire areas of the current collectors 142a and 144a or may also be partially provided at partial areas thereof.

A negative electrode terminal 145a and a positive electrode terminal 145b for electrical connection with outside may be respectively formed in the positive electrode current collector 142a and the negative electrode current collector 144a. Here, the positive electrode terminal 145b and the negative electrode terminal 145a may extend from the positive electrode current collector 142a and the negative electrode current collector 144a and protrude from one side of the cover members 147 and 148 or be exposed through surfaces of the cover members 147 and 148.

Here, the positive electrode active material 142b and the negative electrode active material 144b may contain a polytetrafluoroethylene (PTFE) component. This is to prevent the positive electrode active material 142b and the negative electrode active material 144b from being respectively separated from the current collectors 142a and 144a or to prevent cracks from occurring in the positive electrode active material 142b and the negative electrode active material 144b during banding.

The separator 143 disposed between the positive electrode 142 and the negative electrode 144 may include a nanofiber web layer 143b disposed at one surface or both surfaces of a nonwoven fabric layer 143a.

Here, the nanofiber web layer 143b may be a nanofiber containing one or more selected from polyacrylonitrile nanofiber and polyvinylidene fluoride nanofiber.

Preferably, the nanofiber web layer 143b may be formed of only the polyacrylonitrile nanofiber to secure a radial structure and uniform porosity.

The cover members 147 and 148 are formed of a plate-shaped member having a predetermined area and accommodate the electrode assembly 141 and the electrolyte therein to protect the electrode assembly 141 from an external force.

For this, the cover members 147 and 148 include a pair of a first cover member 147 and a second cover member 148 and are sealed by an adhesive along an edge to prevent exposure and leakage of the electrolyte and the electrode assembly 141 accommodated therein to the outside.

In the case of the cover members 147 and 148, the first cover member 147 and the second cover member 148 may be formed as two members, and then both rims of the first cover member 147 and the second cover member 148, which constitute the sealing portion, may be sealed by an adhesive, or the first cover member 147 and the second cover member 148 may be formed in one piece, and folded in half in a width direction or longitudinal direction, and then the remaining portions, which face each other, may be sealed by an adhesive.

By being formed of the above-described structure, the flexible battery 140 may be freely deformed by an external force.

Although one embodiment of the present invention has been described above, the spirit of the present invention is not limited to the embodiment presented herein. One of ordinary skill in the art who understands the spirit of the present invention may easily propose different embodiments within the scope of the same spirit by addition, modification, omission, or the like of an element, and the different embodiments should also be construed as belonging to the scope of the spirit of the present invention.

INDUSTRIAL APPLICABILITY

The wearable device according to one embodiment of the present invention may be utilized as a heartbeat measuring device whose use time is extended.

The wearable device according to one embodiment of the present invention may be utilized as a smart watch with improved airtightness.

The wearable device according to one embodiment of the present invention may be utilized as a smart band that is wirelessly chargeable.

The invention claimed is:

1. A wearable device comprising:
a body member including a heartbeat sensor;
a first band member and a second band member including an accommodating portion respectively formed at a portion coupled to the body member;
a flexible battery having a predetermined length with a plate shape having a predetermined area;
a circuit board disposed inside the body member and disposed above the flexible battery;
a connecting member having one end coupled to the circuit board and other end disposed below the flexible battery and electrically connected to the heartbeat sensor, and wherein the connecting member includes a portion connected to the heartbeat sensor and protruded toward the flexible battery;
a power receiving antenna disposed at a surface of the connecting member to wirelessly receive power and supply power to the flexible battery, and wherein the power receiving antenna surrounds the portion connected to the heartbeat sensor; and
a shielding sheet disposed between the flexible battery and the power receiving antenna,
wherein the shielding sheet is adhered to the power receiving antenna, and the shielding sheet shields a magnetic field generated by a radio signal induced in the power receiving antenna,
wherein an intermediate portion of the flexible battery is accommodated in the body member and each remaining end of the flexible battery are respectively accommodated in the accommodating portion of the first band member and the second band member; and
wherein the flexible battery is embedded in the body member, the first band member and the second band member such that the flexible battery is simultaneously positioned inside the body member, the first band member and the second band member;
wherein the flexible battery includes:
an electrode assembly, and wherein the electrode assembly includes a positive electrode, a negative electrode and a separator disposed between the positive electrode and the negative electrode; and
a cover member having a plate shape area configured to seal the electrode assembly;
wherein the cover includes a upper cover member covering a upper surface of the negative electrode and a lower cover member covering a lower surface of the positive electrode;
wherein the cover member includes a first pattern for contraction and relaxation in a longitudinal direction when the flexible battery is bent;
wherein the electrode assembly includes a second pattern for contraction and relaxation in a longitudinal direction when the flexible battery is bent;
wherein each of the first pattern and the second pattern includes a plurality of crests and troughs alternately positioned in the longitudinal direction of the cover member and the electrode assembly, and each of the crests and troughs is formed in a direction parallel to a width direction of the cover member and the electrode assembly, and
wherein the crests of the first pattern are formed to correspond to the crests of the second pattern and the troughs of the first pattern are formed to correspond to the troughs of the second pattern; and
wherein the crest of the electrode assembly is arranged between the crest of the upper cover member and the crest of the lower cover member, and
wherein the trough of the electrode assembly is arranged between the trough of the upper cover member and the trough of the lower cover member;
wherein the first pattern and the second pattern have a same behavior.

2. The wearable device of claim 1, wherein a seating portion that includes a portion of the heartbeat sensor is formed at a bottom surface of the body member.

3. The wearable device of claim 1, wherein the power receiving antenna is disposed at the surface opposite a surface of the connecting member connected to the heartbeat sensor.

4. The wearable device of claim 1, wherein the connecting member is a flexible printed circuit board.

5. The wearable device of claim 4, wherein the connecting member is folded at least once such that a portion thereof is disposed between the flexible printed circuit board and the flexible battery.

6. The wearable device of claim 5, wherein a length of the portion of the connecting member disposed between the flexible printed circuit board and the flexible battery is greater than twice a width of the circuit board.

7. The wearable device of claim 1, wherein the power receiving antenna receives power in a magnetic resonance manner or a magnetic induction manner.

8. The wearable device of claim 1, wherein the portion of the flexible battery in the accommodating portion of the first band member and the second band member is entirely or partially corrugated.

9. The wearable device of claim 1, comprising a communication unit configured to transmit heartbeat information measured by the heartbeat sensor.

* * * * *